United States Patent
Maule et al.

(10) Patent No.: US 8,162,876 B2
(45) Date of Patent: *Apr. 24, 2012

(54) MEDICATION INFUSION SET

(75) Inventors: Susie E. Maule, South Pasadena, CA (US); Sheldon B. Moberg, Thousand Oaks, CA (US); Arin N. Holecek, Lakewood, CA (US); Christopher G. Griffin, Sylmar, CA (US); Julian D. Kavazov, Arcadia, CA (US); Paul H. Kovelman, Simi Valley, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 861 days.

This patent is subject to a terminal disclaimer.

(21) Appl. No.: 11/975,315

(22) Filed: Oct. 18, 2007

(65) Prior Publication Data

US 2008/0045891 A1 Feb. 21, 2008

Related U.S. Application Data

(63) Continuation of application No. 11/003,225, filed on Dec. 3, 2004, now Pat. No. 7,303,543.

(51) Int. Cl.
*A61M 31/00* (2006.01)

(52) U.S. Cl. ..................... 604/93.01; 604/533

(58) Field of Classification Search ............... 604/93.01, 604/533, 164.01, 164.04, 158, 192, 264, 604/177
See application file for complete search history.

(56) References Cited

U.S. PATENT DOCUMENTS

| | | |
|---|---|---|
| 4,433,072 A | 2/1984 | Pusineri et al. |
| 4,494,950 A | 1/1985 | Fischell |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |

(Continued)

FOREIGN PATENT DOCUMENTS

EP 1338295 8/2003

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner* — Christopher D Koharski
(74) *Attorney, Agent, or Firm* — Pillsbury Winthrop Shaw Pittman LLP

(57) ABSTRACT

An infusion set is provided for use in delivering fluid through a cannula, which is housed on a cannula housing, to a selected subcutaneous infusion site on a patient. The fluid is generally a medication, for example, insulin. The cannula is in fluid communication with a fluid passageway surrounded by a projection on the cannula housing that includes one or more rail-like extensions acting as connection guides. A connector connects the cannula housing to a fluid delivery system, such as an infusion pump. The connector includes a connecting needle and one or more guide arms that slide over the rail-like extensions to guide the needle into the self-sealing septum. The connector includes one or more locking arms, with barbs at the end, to connect with one or more recesses that are provided in the cannula housing.

25 Claims, 12 Drawing Sheets

U.S. PATENT DOCUMENTS

| | | | |
|---|---|---|---|
| 4,723,947 | A | 2/1988 | Konopka |
| 4,731,726 | A | 3/1988 | Allen, III |
| 4,755,173 | A | 7/1988 | Konopka et al. |
| 4,781,798 | A | 11/1988 | Gough |
| 4,871,351 | A | 10/1989 | Feingold |
| 4,880,412 | A | 11/1989 | Weiss |
| 5,080,653 | A | 1/1992 | Voss et al. |
| 5,097,122 | A | 3/1992 | Colman et al. |
| 5,101,814 | A | 4/1992 | Palti |
| 5,108,819 | A | 4/1992 | Heller et al. |
| 5,165,407 | A | 11/1992 | Wilson et al. |
| 5,257,980 | A | 11/1993 | Van Antwerp et al. |
| 5,262,035 | A | 11/1993 | Gregg et al. |
| 5,262,305 | A | 11/1993 | Heller et al. |
| 5,264,104 | A | 11/1993 | Gregg et al. |
| 5,264,105 | A | 11/1993 | Gregg et al. |
| 5,284,140 | A | 2/1994 | Allen et al. |
| 5,299,571 | A | 4/1994 | Mastrototaro |
| 5,320,725 | A | 6/1994 | Gregg et al. |
| 5,322,063 | A | 6/1994 | Allen et al. |
| 5,356,786 | A | 10/1994 | Heller et al. |
| 5,370,622 | A | 12/1994 | Livingston et al. |
| 5,371,687 | A | 12/1994 | Holmes, II et al. |
| 5,376,070 | A | 12/1994 | Purvis et al. |
| 5,390,671 | A | 2/1995 | Lord et al. |
| 5,391,250 | A | 2/1995 | Cheney, II et al. |
| 5,403,700 | A | 4/1995 | Heller et al. |
| 5,411,647 | A | 5/1995 | Johnson et al. |
| 5,466,465 | A | 11/1995 | Royds et al. |
| 5,482,473 | A | 1/1996 | Lord et al. |
| 5,497,772 | A | 3/1996 | Schulman et al. |
| 5,522,803 | A * | 6/1996 | Teissen-Simony ........... 604/177 |
| 5,543,326 | A | 8/1996 | Heller et al. |
| 5,545,143 | A | 8/1996 | Fischell |
| 5,545,152 | A | 8/1996 | Funderburk et al. |
| 5,569,186 | A | 10/1996 | Lord et al. |
| 5,584,813 | A | 12/1996 | Livingston et al. |
| 5,586,553 | A | 12/1996 | Halili et al. |
| 5,593,852 | A | 1/1997 | Heller et al. |
| 5,660,163 | A | 8/1997 | Schulman et al. |
| 5,665,065 | A | 9/1997 | Colman et al. |
| 5,665,222 | A | 9/1997 | Heller et al. |
| 5,750,926 | A | 5/1998 | Schulman et al. |
| 5,779,665 | A | 7/1998 | Mastrototaro et al. |
| 5,791,344 | A | 8/1998 | Schulman et al. |
| 5,904,708 | A | 5/1999 | Goedeke |
| 5,917,346 | A | 6/1999 | Gord et al. |
| 5,954,643 | A | 9/1999 | VanAntwerp et al. |
| 5,965,380 | A | 10/1999 | Heller et al. |
| 5,968,011 | A | 10/1999 | Larsen et al. |
| 5,972,199 | A | 10/1999 | Heller et al. |
| 5,999,848 | A | 12/1999 | Gord et al. |
| 5,999,849 | A | 12/1999 | Gord et al. |
| 6,017,328 | A | 1/2000 | Fischell et al. |
| 6,043,437 | A | 3/2000 | Schulman et al. |
| 6,056,718 | A | 5/2000 | Funderburk et al. |
| 6,074,371 | A | 6/2000 | Fischell |
| 6,081,736 | A | 6/2000 | Colvin et al. |
| 6,083,710 | A | 7/2000 | Heller et al. |
| 6,086,575 | A | 7/2000 | Mejslov |
| 6,088,608 | A | 7/2000 | Schulman et al. |
| 6,103,033 | A | 8/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,123,690 | A | 9/2000 | Mejslov |
| 6,134,461 | A | 10/2000 | Say et al. |
| 6,143,164 | A | 11/2000 | Heller et al. |
| 6,162,611 | A | 12/2000 | Heller et al. |
| 6,175,752 | B1 | 1/2001 | Say et al. |
| 6,213,996 | B1 | 4/2001 | Jepson et al. |
| 6,259,937 | B1 | 7/2001 | Schulman et al. |
| 6,302,866 | B1 * | 10/2001 | Marggi ........... 604/174 |
| 6,329,161 | B1 | 12/2001 | Heller et al. |
| 6,355,021 | B1 | 3/2002 | Nielsen et al. |
| 6,472,122 | B1 | 10/2002 | Schulman et al. |
| 6,484,046 | B1 | 11/2002 | Say et al. |
| 6,488,663 | B1 | 12/2002 | Steg |
| 6,503,381 | B1 | 1/2003 | Gotoh et al. |
| 6,514,718 | B2 | 2/2003 | Heller et al. |
| 6,520,938 | B1 | 2/2003 | Funderburk et al. |
| 6,554,798 | B1 | 4/2003 | Mann et al. |
| 6,558,320 | B1 | 5/2003 | Causey et al. |
| 6,560,471 | B1 | 5/2003 | Heller et al. |
| 6,565,509 | B1 | 5/2003 | Say et al. |
| 6,572,586 | B1 * | 6/2003 | Wojcik ........... 604/165.01 |
| 6,579,690 | B1 | 6/2003 | Bonnecaze et al. |
| 6,591,125 | B1 | 7/2003 | Buse et al. |
| 6,592,745 | B1 | 7/2003 | Feldman et al. |
| 6,605,200 | B1 | 8/2003 | Mao et al. |
| 6,605,201 | B1 | 8/2003 | Mao et al. |
| 6,607,658 | B1 | 8/2003 | Heller et al. |
| 6,616,819 | B1 | 9/2003 | Liamos et al. |
| 6,618,934 | B1 | 9/2003 | Feldman et al. |
| 6,623,501 | B2 | 9/2003 | Heller et al. |
| 6,654,625 | B1 | 11/2003 | Say et al. |
| 6,671,554 | B2 | 12/2003 | Gibson et al. |
| 6,676,816 | B2 | 1/2004 | Mao et al. |
| 6,689,265 | B2 | 2/2004 | Heller et al. |
| 6,733,471 | B1 | 5/2004 | Ericson et al. |
| 6,746,582 | B2 | 6/2004 | Heller et al. |
| 6,749,740 | B2 | 6/2004 | Liamos et al. |
| 6,809,653 | B1 | 10/2004 | Mann et al. |
| 6,881,551 | B2 | 4/2005 | Heller et al. |
| 6,893,545 | B2 | 5/2005 | Gotoh et al. |
| 6,916,159 | B2 | 7/2005 | Rush et al. |
| 6,932,894 | B2 | 8/2005 | Mao et al. |
| 6,942,518 | B2 | 9/2005 | Liamos et al. |
| 7,214,207 | B2 | 5/2007 | Lynch et al. |
| 7,220,241 | B2 | 5/2007 | Csincsura et al. |
| 2002/0082665 | A1 | 6/2002 | Haller et al. |
| 2002/0161288 | A1 | 10/2002 | Shin et al. |
| 2002/0173748 | A1 | 11/2002 | McConnell et al. |
| 2003/0078560 | A1 | 4/2003 | Miller et al. |
| 2003/0088166 | A1 | 5/2003 | Say et al. |
| 2003/0152823 | A1 | 8/2003 | Heller et al. |
| 2003/0176183 | A1 | 9/2003 | Drucker et al. |
| 2003/0176852 | A1 | 9/2003 | Lynch et al. |
| 2003/0181874 | A1 | 9/2003 | Bressler et al. |
| 2003/0188427 | A1 | 10/2003 | Say et al. |
| 2003/0199744 | A1 | 10/2003 | Buse et al. |
| 2003/0220552 | A1 | 11/2003 | Reghabi et al. |
| 2004/0061232 | A1 | 4/2004 | Shah et al. |
| 2004/0061234 | A1 | 4/2004 | Shah et al. |
| 2004/0064133 | A1 | 4/2004 | Miller et al. |
| 2004/0064156 | A1 | 4/2004 | Shah et al. |
| 2004/0074785 | A1 | 4/2004 | Holker et al. |
| 2004/0093167 | A1 | 5/2004 | Braig et al. |
| 2004/0111017 | A1 | 6/2004 | Say et al. |
| 2004/0116864 | A1 | 6/2004 | Boudreaux |
| 2004/0158207 | A1 | 8/2004 | Hunn et al. |
| 2004/0236287 | A1 | 11/2004 | Swenson et al. |
| 2005/0214585 | A1 | 9/2005 | Bernatz et al. |

FOREIGN PATENT DOCUMENTS

| | | |
|---|---|---|
| WO | WO 96/37246 A1 | 11/1996 |
| WO | WO 02/058537 A2 | 8/2002 |

OTHER PUBLICATIONS

Abel et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'-dimethylferrocene mediated glucose biosensor,"Analytica Chim. Acta.,1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and its Applications as a Glucose Sensor," Sensors and Actuators, 1989, pp. 49-70, vol. 18.

Gorton et al., "Amperometric glucose senosrs based on immobilized glucose-oxidizing enzymes and chemically modified electrodes," Analytica Chim Acta., 1991, pp. 43-54, v. 249.

Gorton et al., "Amperometric biosensors based on an apparent direct electron transfer between electrodes and immobilized peroxidases," Analyst, 1992, pp. 1235-1241, vol. 117.

Gough et al., "Two-Dimensional Enzyme Electrode Sensor for Glucose," Analytical Chemistry, 1985, pp. 2351-2357, vol. 57.

Gregg et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

Johnson et al., "In vivo evaluation of an electroenzymatic glucose sensor implanted in subcutaneous tissue," Biosensors & Bioelectronics, 1992, pp. 709-714, vol. 7.

Jonsson et al., "An Electrochemical Sensor for Hydrogen Peroxide Based on Peroxidase Adsorbed on a Spectrographic Graphite Electrode," Electroanalysts, 1989, pp. 465-468, v.1.

Kanapieniene et al., "Miniature glucose biosensor with extended linearity," Sensors and Actuators, 1992, pp. 37-40, vol. B, No. 10.

Kawamori et al., "Perfect Normalization of Excessive Glucagon Responses to Intravenous Arginine in Human Diabetes Mellitus With . . . ," Diabetes, 1980, pp. 762-765, vol. 29.

Kimura et al., "An immobilized Enzyme Membrane Fabrication Method using an Ink Jet Nozzle," Biosensors, 1988, pp. 41-52, vol. 4.

Koudelka et al., "In-vivio Behaviour of Hypodermically Implanted Microfabricated Glucose Sensors," Biosensors & Bioelectronics, 1991, pp. 31-36, vol. 6.

Mastrototaro et al., "An electroenzymatic glucose sensor fabricated on a flexible substrate," Sensors and Actuators, 1991, pp. 139-144, vol. 5.

Mastrototaro et al., "An Electroenzymatic Sensor Capable of 72 Hour Continuous Monitoring of Subcutaneous Glucose," 14th Int'l Diabetes Federation Congress, 1991.

McKean et al., "A Telemetry-Instrumentation System for Chronically Implanted Glucose and Oxygen Sensors," IEEE Transactions on Biomedical Eng., 1988, pp. 526-532, vol. 35, No. 7.

Monroe, "Novel implantable glucose sensors," ACL, 1989, pp. 8-16.

Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n. 2.

Nakamado et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. of NIDDM . . . , 1994, p. 353-358, No. 1057.

Shichiri et al., "An artificial endocrine pancrease—problems awaiting solutions for long term clinical applications of . . . ," Frontiers Med. Biol. Eng., 1991, pp. 283-292, v.3.

Shichiri et al., "Wearable Artificial Endocrine Pancreas with Needle-Type Glucose Sensor," The Lancet, 1982, pp. 1129-1131, vol. 2 (8308).

Shichiri et al., "Telemetry Glucose Monitoring Device with Needle-Type Glucose Sensor," Diabetes Care, May-Jun. 1986, pp. 298-301, vol. 9, No. 3.

Shichiri et al., "Normalization of the Paradoxic Secretion of Glucagen in Diabetics Who Were Controlled by the Artificial Beta Cell," Diabetes, 1979, pp. 272-275, vol. 28.

Shichiri et al., "Closed-Loop Glycemic Control with a Wearable Artificial Endocrine Pancreas," Diabetes, 1984, pp. 1200-1202, vol. 33.

Shichiri et al., "In Vivo Characteristics of Needle-Type Glucose Sensor," Hormone and Metabolic Research, 1988, pp. 17-20, vol. 20.

Shichiri et al., "A Needle-Type Glucose Sensor," Life Support Systems: The Journal of the European Society for Artificial Organs, 1984, pp. 7-9, vol. 2, supplement 1.

Shichiri et al., "The Wearable Artificial Endocrine Pancreas with a Needle-Type Glucose Sensor," Acta Pediatr, Jpn, 1984, pp. 358-370, vol. 26.

Shichiri et al., "Glycaemic Control in Pancreatectomized Dogs with a Wearable Artificial Endocrine Pancreas," Diabetologica, 1983, pp. 179-184, vol. 24.

Shichiri et al., "Membrane design for extending the long-life of an implantable glucose sensor," Diab. Nutr. Metab., 1989, pp. 309-313, vol. 2.

Shinkai et al., "Molecular Recognition of Mono- and Di-Saccharides by Phenylboronic Acids in Solvent Extraction and as a Monolayer," J. Chem. Soc., 1991, pp. 1039-1041.

Tamiya et al., "Micro Glucose Sensors Using Electron Mediators Immobilized on a Polypyrrole-Modified Electrode," Sensors and Actuators, 1989, pp. 297-307, v.18.

Tsukagoshi et al., "Specific Complexation with Mono- and Disaccharides That Can Be Detected by Circular Dichroism," J. Org. Chem., 1991, pp. 4089-4091, vol. 56.

Urban et al., "Minaturized multi-enzyme biosensors integrated with pH sensors on flexible polymer carriers . . . ," Biosensors & Bioelectronics, 1992, pp. 733-739, vol. 7.

Urban et al., "Miniaturized thin-film biosensors using covalently immobilized glucose oxidase," Biosensors & Bioelectronics, 1991, pp. 555-562, vol. 6.

Velho et al., "In vivo calibration of a subcutaneous glucose sensor for determination of subcutaneous glucose kinetics," Diab. Nutr. Metab., 1988 pp. 227-233, v.3.

Yokoyama et al., "Integrated Biosensor for Glucose and Galactose," Analytica Chimica Acta, 1989, pp. 137-142, vol. 218.

Nishida et al., "Development of a ferrocene-mediated needle-type glucose sensor . . .," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinica Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n. 5.

Jobst et al., "Thin-Film Microbiosensors for Glucose-Lactate Monitoring," Anal. Chem., 1996, p. 3173-79, vol. 68.

Shults et al., "A Telemetry-Instrumentation System for Monitoring Multiple Subcutaneously Implanted Glucose Sensors," IEEE Trans. on Biomed. Eng., 1994, pp. 937-942, v41, n. 10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-77, vol. 65.

Bindra et al., "Design and in Vitro Studies of a Needle-Type Glucose Sensor for Subcutaneous Monitoring," Anal. Chem., 1991, pp. 1692-1696, vol. 63.

Boguslavsky et al., "Applications of redox polymers in biosensors," Solid State Ionics, 1993, pp. 189-197, vol. 60,.

Geise et al., "Electropolymerized 1,3-diaminobenzene for the construction of a 1-1'-dimethylferrocene mediated glucose blosensor,"Analytica Chim. Acta., 1993, pp. 467-473, v18.

Jonsson et al., "An Electrochemical Sensor for Hydrogen Peroxide Based on Peroxidase Absorbed on a Spectrographic Graphite Electrode," Electroanalysts, 1989, pp. 465-468, v.1.

Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.

Urban et al., "Miniaturized thin-film biosensors using covalently immobilized glucose oxidase," Biosensors & Bioeleotronics, 1991, pp. 555-562, vol. 6.

Shults et al., "A Telemetry-Instrumentation System for Monitoring Multiple Subcutaneously Implanted Glucose Sensors," IEEE Trans. on Biomed. Eng., 1994, pp. 937-942, v41, n.10.

Nishida et al., "Development of a ferrocene-mediated needle-type glucose sensor . . . ," Medical Process Through Technology, 1995, pp. 91-103, vol. 21.

Hashigushi et al., "Development of a Miniaturized Glucose Monitoring System by Combining a Needle-Type Glucose Sensor . . . ," Diabetes Care, 1994, pp. 387-389, v.17, n.5.

Jobst et al., "Thin-Film Microbiosensors for Glucose-Lactate Monitoring," Anal. Chem., 1996, p. 3173-3179, vol. 68.

\* cited by examiner

MEDICATION INFUSION SET

RELATED APPLICATION DATA

This application is a continuation of U.S. patent application Ser. No. 11/003,225, filed Dec. 3, 2004, now U.S. Pat. No. 7,303,543.

BACKGROUND OF THE INVENTION

1. Field of the Invention

This invention relates generally to an infusion set for subcutaneous delivery of a selected medication or other fluid to a patient. More particularly, this invention relates to an improved infusion set having a cannula housing and a connector for connecting the cannula housing to a delivery device.

2. Description of Related Art

Infusion sets are typically used for delivering a selected medication or other fluid to a patient. Infusion sets may include a cannula, which may be relatively soft and flexible. The cannula provides a transcutaneous passageway to administer a medication or other fluid to a subcutaneous site on a patient. The cannula generally attached to a cannula housing, which may be placed on the skin of the patient when the cannula is inserted. A connector attaches to the cannula housing to connect the cannula to the fluid delivery system. The fluid delivery system is generally placed in fluid communication with the connector by way of a length of infusion tubing. Examples of fluid delivery systems are shown in U.S. Pat. Nos. 4,562,751, 4,685,903, 5,080,653, 5,097,122, which are herein incorporated by reference.

Infusion sets of the type described above are generally used to deliver medication, such as insulin, to a patient over an extended period of time. The infusion sets usually are adapted to rest on the skin of the patient. The cannula housing may remain on the patient's skin for several days, and the patient may disconnect the connector when performing certain activities, like showering. Because a patient changes infusion sets fairly frequently, it is beneficial to have an infusion set that is easy to insert, easy to connect properly, and easy to remove and dispose of.

An infusion set of the above type is described in U.S. Pat. No. 5,522,803. The infusion set comprises a cannula housing with a cannula and a needle holder to be connected to the cannula housing. The cannula housing includes two guide openings and two locking openings with shoulders for engaging barbs on locking pins of the needle holder. The needle holder includes guide pins that co-operate with the guide openings on the cannula housing. The needle on the needle holder is guided by the guide pins into the cannula housing so that the needle penetrates a membrane at the inlet of a fluid passageway of the cannula housing. The fluid passageway is in fluid communication with the cannula. Thus, when the needle penetrates the membrane, the fluid may flow through the connector into the cannula housing and then into the patient. The guide pins must be guided carefully into the guide openings, as the guide openings surround the pins on all four sides when the cannula housing and needle holder are guided together.

Another infusion set of the above type is described in U.S. Pat. No. 6,302,866. The infusion set comprises a cannula housing with a cylindrical extension and a needle holder with a guide sleeve that closely slides over the cylindrical extension. The connection must be done carefully, because the cylindrical extension fits closely into the guide sleeve. The guide sleeve surrounds a connecting needle that is guided into the passageway of the cylindrical extension. The passageway in the cylindrical extension is in fluid communication with the cannula and has a septum at its inlet that is pierced by the connecting needle. Once the septum is pierced, fluid can flow from an infusion device through the needle holder into the cannula housing and then into the patient.

BRIEF SUMMARY OF THE INVENTION

In accordance with the invention, an infusion set is provided for use in delivering fluid through a cannula to a selected subcutaneous infusion site on a patient. The fluid is generally a medication, for example, insulin. The cannula is a soft and flexible cannula and is supported by a cannula housing. The cannula housing also includes a fluid passageway in fluid communication with the cannula. At one end of the fluid passageway is a self-sealing septum. The fluid passageway is surrounded by a projection on the cannula housing that includes one or more rail-like extensions acting as connection guides. The rail-like extensions may be substantially triangular or otherwise suitably shaped to act as guides. The cannula housing also includes a base that rests upon a patient's skin when the cannula is inserted into the skin.

The infusion set also includes a connector that connects the cannula housing to fluid tubing that allows fluid to flow from a fluid source, which may be a fluid delivery system, such as an infusion pump, through the connector to the cannula housing and through the cannula into the patient. The connector includes a connecting needle that is mounted thereon to pierce the self-sealing septum on the cannula housing to allow flow of fluid through the needle into the fluid passageway. The connecting needle is in fluid communication with the fluid tubing. The connector also includes one or more guide arms that slide over the rail-like extensions to guide the needle into the self-sealing septum. The connector includes one or more locking arms, with barbs at the end, to connect with one or more recesses that are provided in the cannula housing. Once the barbs are pushed into the recesses, the connector is essentially locked in place with respect to the cannula housing. The connector is preferably reversible so that it may be connected to the cannula housing regardless of which side is up.

The cannula housing is inserted into the skin using an introducer. The introducer has the same guide arms and locking arms as the connector. It includes an introducing needle that passes through the self-sealing septum and fluid passageway of the cannula housing and into the cannula. When connected to the cannula housing, the tip of the introducing needle is outside the cannula.

A method of delivery of a fluid is provided comprising positioning a cannula housing according to the invention at an infusion site on a patient and engaging the cannula housing with a connector according to the invention. The positioning of the cannula housing may include using an introducer according to the invention to pierce the skin of the patient, and removing the introducer from the cannula housing once the cannula housing is positioned on the infusion site.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION OF THE INVENTION

In the following description, reference is made to the accompanying drawings which form a part hereof and which illustrate several embodiments of the present invention. It is understood that other embodiments may be utilized and structural and operational changes may be made without departing from the scope of the present invention.

Figure 1:
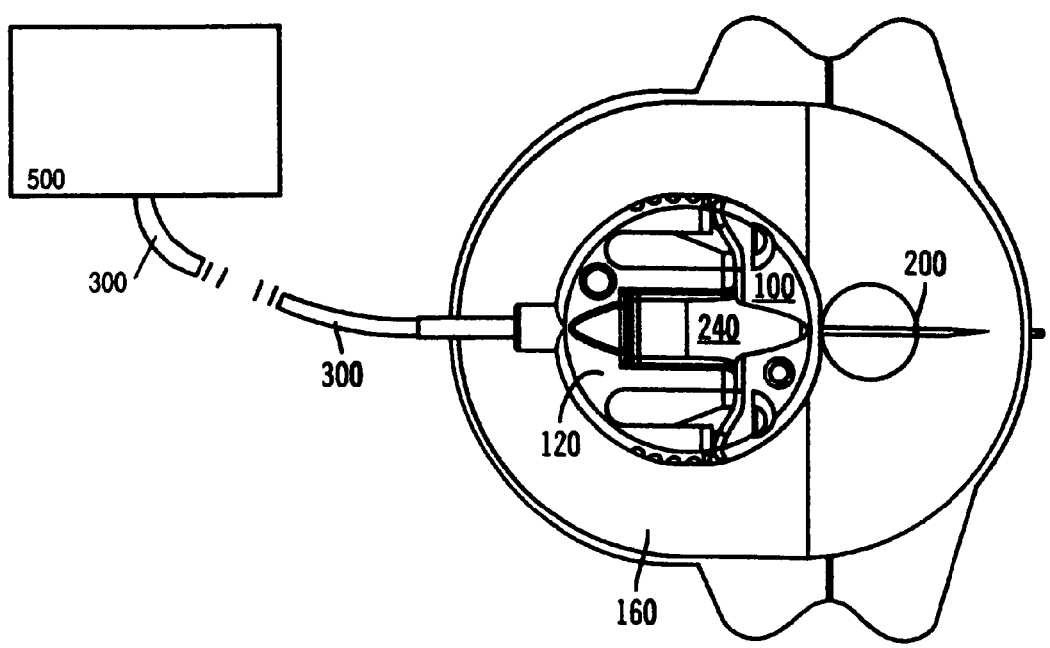
FIG. 1 is a perspective view of a cannula housing and connector in connected form in accordance with an embodiment of the invention.
Figure 2:
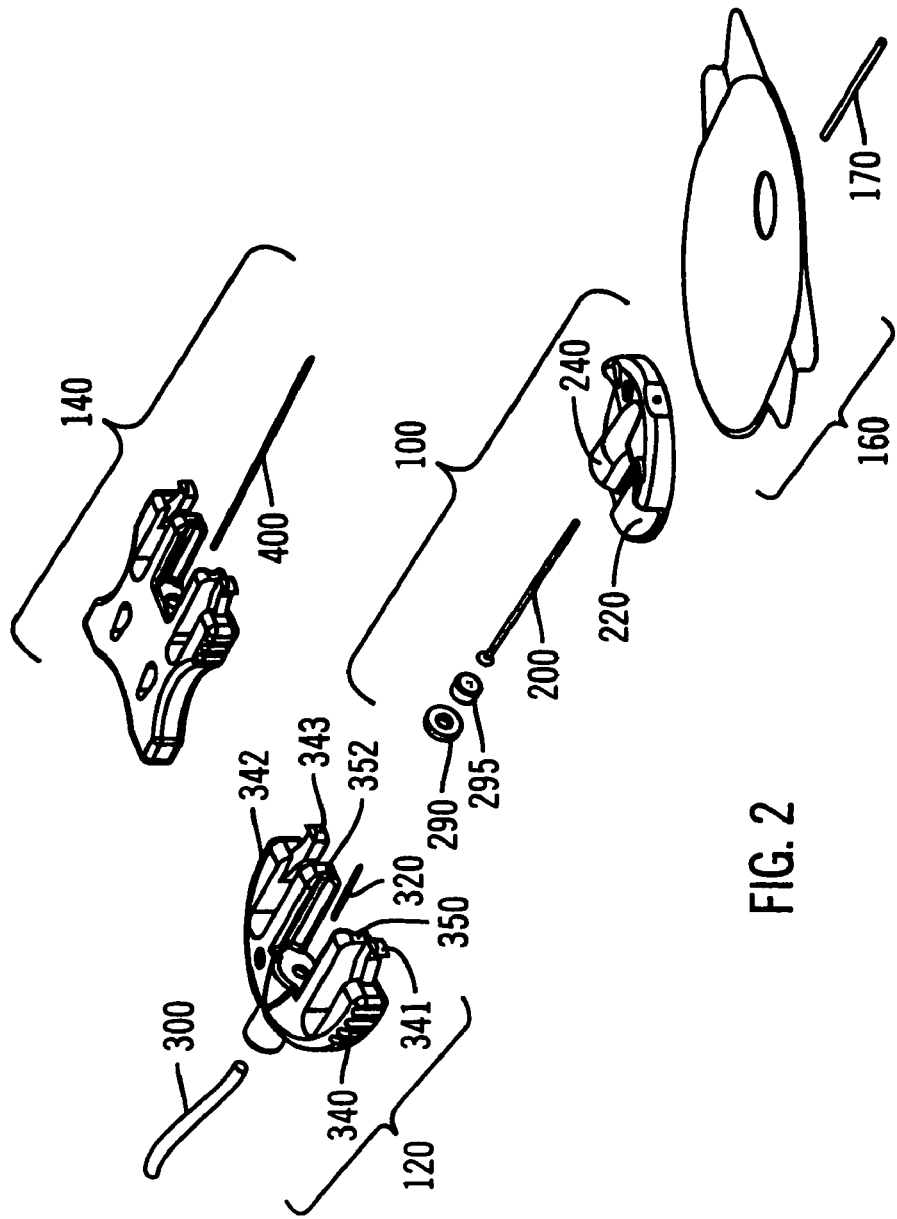
FIG. 2 is perspective view of a cannula housing, connector, introducer, and internal components in accordance with an embodiment of the invention in an exploded view.
Figure 3:
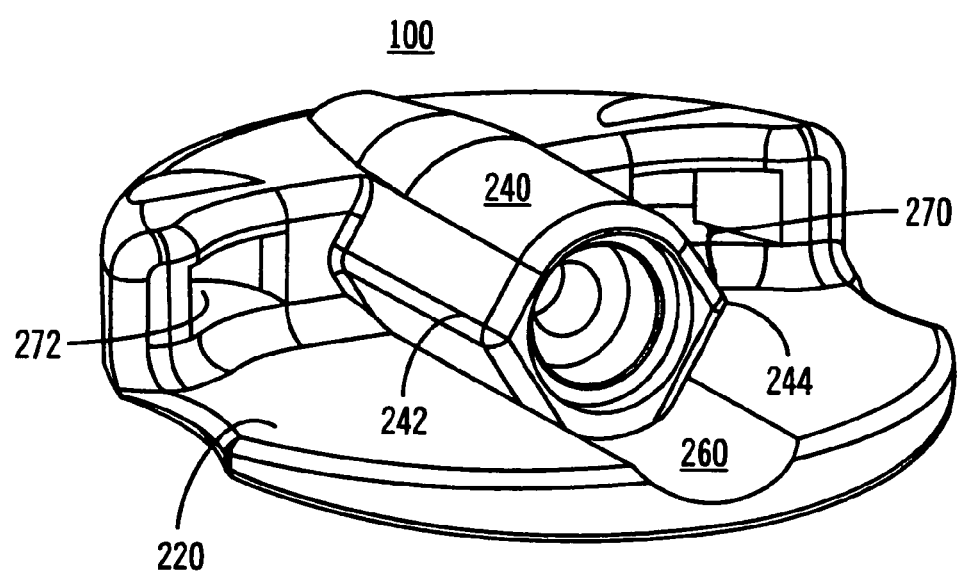
FIG. 3 is a perspective view of a cannula housing in accordance with an embodiment of the invention.

As shown in FIGS. 1-3, the infusion set comprises a cannula housing 100 and a connector 120. The cannula housing 100 carries a soft and flexible cannula 200. The cannula 200 may be tapered at the end. Any flexible tubing may be used for the cannula, provided that is biocompatible and insulin compatible. For example, but without limitation, the cannula 200 may be composed of polytetrafluoroethylene (PTFE) or fluorinated ethylene propylene (FEP). The cannula housing 100 has a base 220 that rests upon the patient's skin when the cannula 200 is inserted into the patient. The base 220 may be attached to the patient's skin, for example by an adhesive patch. Although the base 220 is shown as at least partially circular in nature, it may be square, rectangular or any other shape that is desired. A projection 240 of the cannula housing 100 surrounds a fluid passageway (not shown) that is in fluid communication with the cannula 200. At the end of the fluid passageway opposite the cannula is a septum 295. This may be a self-sealing septum, for example a substantially barrel-shaped, such as a beer-barrel shaped, self-sealing septum. The septum may also be substantially shaped like a disc or a ball, or any other preferable shape.

The projection 240 is generally at least partially attached along its length to the base 220. However, the projection 240 may be entirely separate from the base 220 along its length, allowing a space between the projection 240 and the base 220. The end of the projection 240 opposite the end with the septum 295 would still be attached to remainder of the cannula housing 100, such that the cannula housing 100 is still only one integral piece. The base 220 may also have a groove 260 cut into it to allow for a higher projection without the need for the entire cannula housing 100 to be taller. The projection 240 may have a relatively flat top, which can also reduce the height of the cannula housing 100 and of the infusion set and can reduce the overall volume of the infusion set. When the infusion set is thinner, it can have a lower profile and be less noticeable.

The two sides of the projection 240 on the cannula housing 100 are rail-like extensions or guide rails 242 and 244. These guide rails 242 and 244 may be substantially triangular, as shown, but they may be shaped in any other configuration that allows for guiding of the connector 120 onto the cannula housing 100. For example, they could be rectangular or peg-shaped. At the side of the cannula housing 100 near the cannula 200, there are two recesses 270 and 272 formed to receive barbs that are on locking arms of the connector. These guide rails are visible to the user, making the infusion set easier to connect. Additionally, the base of the cannula housing assists in guiding the needle, acting as a bottom boundary for a connector. The cannula is preferably angled so that the cannula is inserted into the skin at an angle. The fluid passageway and connector fluid passageway may each be similarly angled. If both are angled to match the cannula, the passage of fluid will be one straight line from the point at which the fluid enters the connector until the end of the cannula, where the fluid enters the patient's body.

Figure 4:
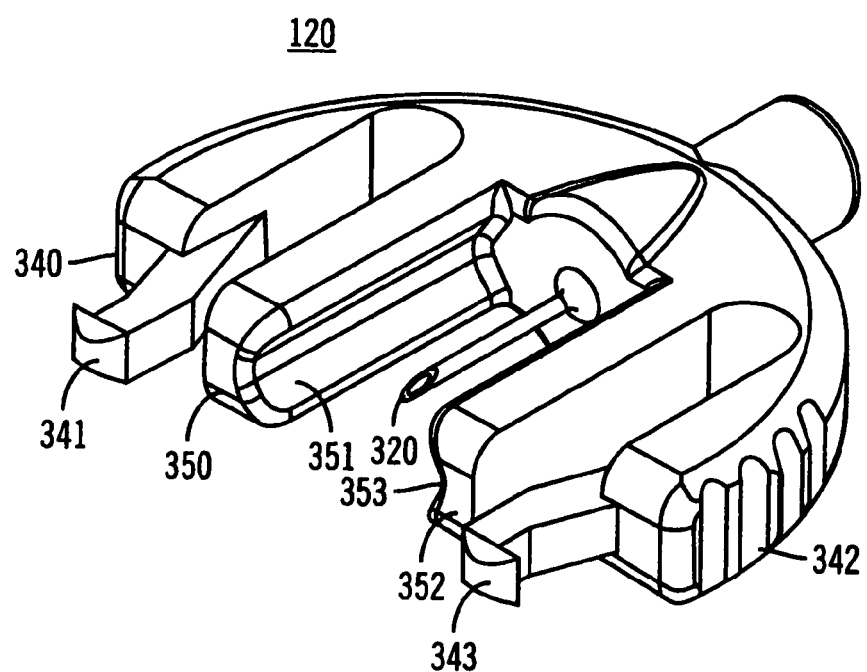
FIG. 4 is a perspective view of a connector in accordance with an embodiment of the invention.

As shown in FIGS. 1, 2 and 4, the connector 120 connects the cannula housing 100 to fluid tubing 300, which allows fluid to flow from a fluid source, which may be a fluid delivery system, such as an infusion pump 500 (as shown in FIG. 1), to the connector 120. The connector 120 includes a connecting needle 320, which is in fluid communication with the fluid tubing 300. Inside the connector 120, a connector fluid passageway allows the connecting needle 320 to be in fluid communication with the fluid tubing 300. The connector 120 has two locking arms 340 and 342, with barbs 341 and 343 on each that are received by the recesses 270 and 272 on the cannula housing 100. There may be grips on one or more edges of the locking arms 340 and 342 for facilitating grasping by the user. When the barbs 341 and 343 are engaged with the recesses 270 and 272, the connector 120 is essentially locked into the cannula housing 100. To disconnect the connector 120 from the cannula housing 120, the user pushes the locking arms 340 and 342 toward each other and releases the barbs 341 and 343 from the recesses 270 and 272. Alternatively, the locking arms 340 and 342 may be formed as levers, which would allow the ends of the locking arms to release outwardly when the user pressed on the ends opposite the barbs. It is also possible to remove one of the locking arms entirely or to replace one locking arm with an arm that does not latch or lock into the cannula housing. In such an embodiment, only one locking arm would lock into the cannula housing. As another alternative, the locking arms may have alternative locking structures to barbs, such as clips or other connecting pieces.

On either side of the needle 320 on the connector 120 are guide arms 350 and 352. The guide arms 350 and 352 extend alongside and past the needle 320. Because the guide arms 350 and 352 extend past the needle 320, it is difficult for the user to be injured by, or to injure, the needle 320 when the connector 120 is separated from the cannula housing 120. The guide arms 350 and 352 have indentations 351 and 353 that match the guide rails 242 and 244 of the projection 240 of the connector 120. For example, if the guide rails 242 and 244 are triangular in shape, the guide arms 350 and 352 will have triangular indentations. When the user connects the connector 120 to the cannula housing 100, the guide arms 350 and 352 slide along the projection 240, guiding the needle 320 into the fluid passageway of the cannula housing 100.

The connector is preferably symmetrical, so that it is reversible and may be placed into the connector with either of its top or bottom facing upward. If the connector is symmetrical, the patient does not have to worry about which way to place the connector. This will allow for quicker and easier connection.

Figure 1A:
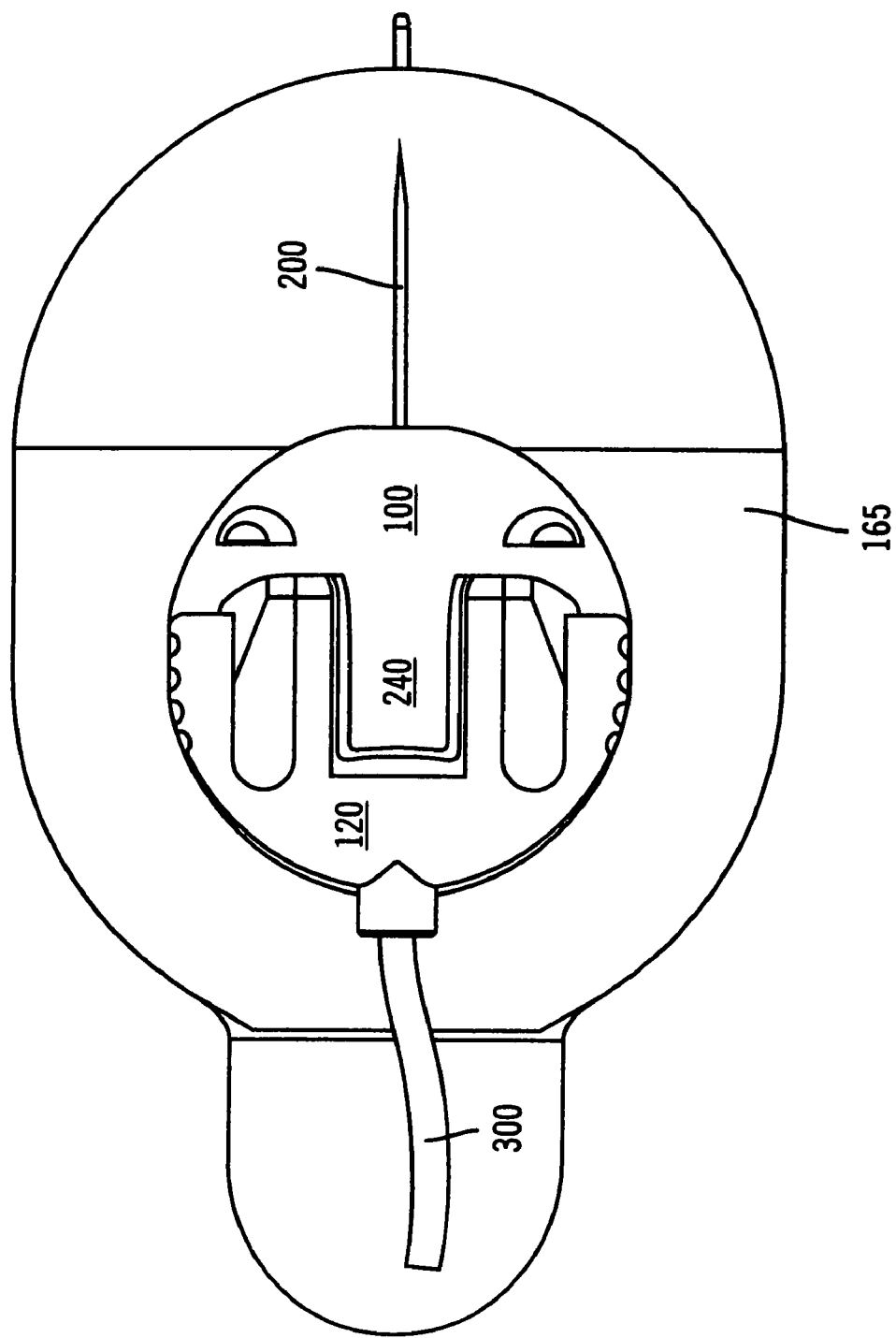
FIG. 1A is a top view of a cannula housing and connector in connected form in accordance with an embodiment of the invention.

The cannula housing may be adhered to the patient's skin by an adhesive. The adhesive may be on a patch that is attached to the base of the cannula housing. In one embodiment, as shown in FIGS. 1, 1A and 2, the adhesive is covered with a one or more piece liner 160 (or 165 in FIG. 1A) that the patient removes to release the adhesive side. The liner 160 protects the adhesive from being removed or from attaching to anything else until the patient wishes to use the infusion set. The liner can also keep the adhesive layer relatively sterile. As shown in FIGS. 1 and 2, the adhesive may be on a flat patch that is attached to the base. Alternatively, the adhesive may be folded, as shown in FIG. 1A. In the folded configuration, the patient removes a small liner piece from the unfolded portion of the patch. The patient then inserts the cannula into the skin. Afterward, the user pulls the liner off of the folded portion of the patch, allowing it to lie flat on the user's skin. In either configuration, the patch may be colored, patterned, or a combination of both. In the folded configuration, the small liner piece from the unfolded portion may have a color and/or pattern that is different from the color and/or pattern on the folded portion to more easily differentiate between the two liners.

Figure 5:
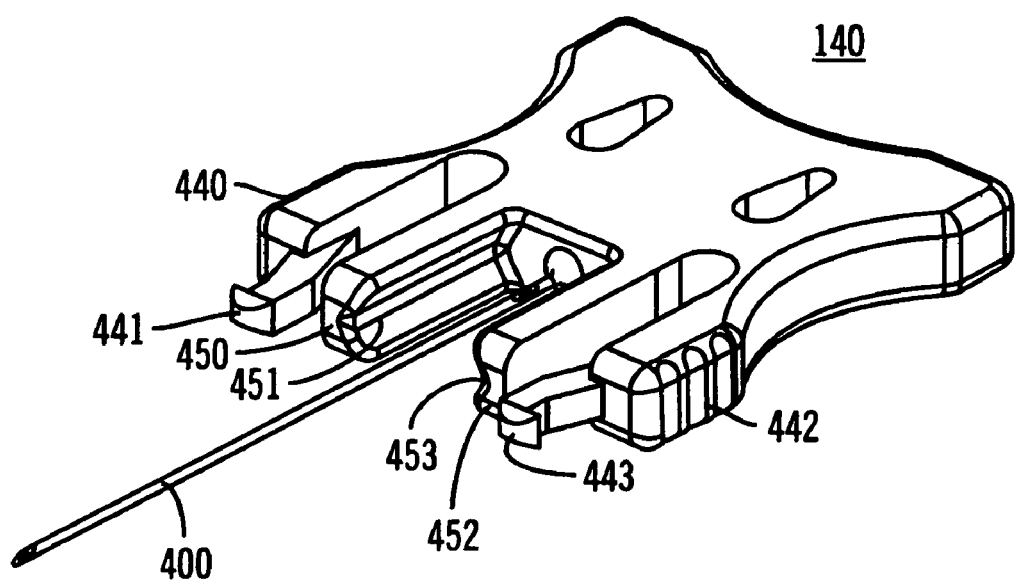
FIG. 5 is a perspective view of an introducer in accordance with an embodiment of the invention.

To insert the cannula into the patient, an introducer may be used. As shown in FIGS. 2 and 5, the introducer 140 has guide arms 450 and 452 and locking arms 440 and 442 that are shaped the same as those on the connector 120. However, the introducer needle 400 is much longer than the needle on the connector. The introducer needle 400 is long enough that when the introducer 140 is connected to the cannula housing 100, the tip of the introducer needle 400 extends beyond the cannula 200. The introducer needle 400 may be affixed to the introducer 140 by a UV or other type of adhesive, by welding, by a molding process, or by any other suitable process. To insert the cannula 200 into the patient, the user grips the joined introducer 140 and cannula housing 100 and inserts the tip of the introducer needle 400 into the patient. The introducer needle 400 and cannula 200 are pushed into the patient, so that the cannula 200 is almost entirely under the skin of the patient. The cannula housing 100 is preferably affixed to the patient's outer skin, and the introducer 140 is unlocked and removed from the cannula housing 100. The connector 120 can then be inserted and locked into the cannula housing 100 so that fluid may be infused into the patient. In further embodiments, rubber grips may be overmolded onto the grips of the introducer and/or the connector to improve ability to grasp the introducer and/or connector. In addition, rubber overmold may be added to the cannula housing 100 to improve the user's ability to grasp the part during removal of the introducer 140 or connector 120.

The cannula housing 100 can be packaged connected to the introducer. To protect the patient from injury from the needle, a needle guard may cover the introducer needle, which extends beyond the cannula. The needle guard may be a small plastic tube that covers the needle and some or all of the cannula. If a small plastic tube is used as a needle guard, it may be colored so that it is easily visible. Thus, the patient easily would be able to see if the needle guard is in place. The small plastic tube may have only holes at each end of the tube. Alternatively, it may be slit down the side for ease of removal and replacement. A slit guard may reduce damage to the cannula 200 caused by attempting to slide the small plastic tube onto the needle and cannula. A larger needle cover may also be used. The larger needle cover may connect or snap to the cannula housing. It may also act as a cover for the introducer after insertion of the cannula, when the introducer is removed from the cannula housing.

The cannula housing may be made out of a plastic, such as an acrylic or polypropylene or polycarbonate. A polycarbonate cannula housing may be transparent, so that the patient can see whether any bubbles are present in the fluid passageway. The connector may also be made out of a plastic, such as an acrylic or polypropylene or polycarbonate. As in the cannula housing, a polycarbonate connector may be transparent, so that the patient can see whether any bubbles are present in the connector fluid passageway. The plastics used for the cannula housing and the connector should be compatible with the medication or fluid selected for delivery through these parts and should pass the required biological tests for skin contact.

The patch or infusion set itself may be time-sensitive, to indicate to the patient when it is time to remove the infusion set. A time-sensitive indicator may be chemical, mechanical, or electrical. The patch itself, a portion of the patch, the infusion set, or a portion of the infusion set may contain an ink that changes color or appearance with passage of time. An infusion set is typically used for a minimum of 3 days, but may be adapted to be used for any predetermined period of time. Similarly, the time-sensitive indicator may be designed to be used for any predetermined period of time. Alternatively, a different colored patch may be used for a different day of the week, meaning the first and/or last day for the infusion set, so that the user will easily know when to change the infusion set. For example, if the color red means the first day for the set is Monday and the last day is set for Wednesday, the user will know to insert the infusion set on Monday and to remove it on Wednesday. Graphics and other designs may also be printed on the patches.

Figure 6:
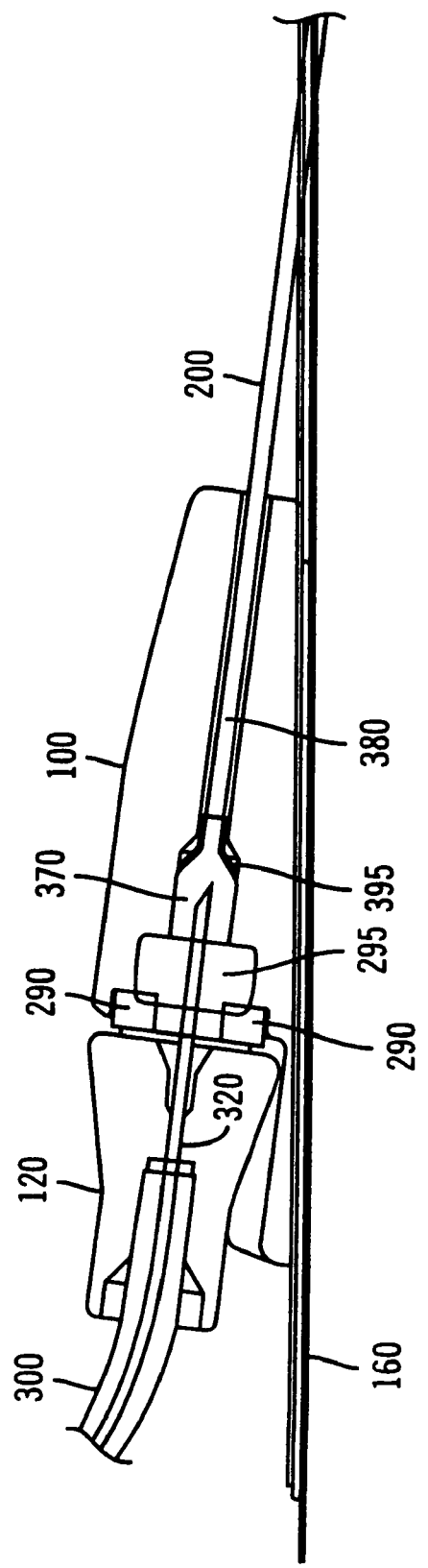
FIG. 6 is a horizontal sectional view of a cannula housing and connector in connected form in accordance with an embodiment of the invention.

FIG. 6 is a cutaway view of the infusion set comprising the cannula housing 100 and the connector 120. The connecting needle 320 has pierced the substantially beer-barrel shaped septum 295 to allow flow from the fluid tubing 300 into the fluid passageway 380. At the end of the cannula housing 100, past the beer-barrel shaped septum 295 there may be a washer 290, which can assist in holding the beer-barrel shaped septum 295 in place and provide compression to the septum to create a seal. The washer 290 may be made of suitable materials, for example metal or plastic. The washer 290 may be welded to the connector to retain the septum 295. A needle guide 395 may be used to align the needle with the fluid passageway 380. The needle guide 395 may be a metal guide or a plastic guide. To seal the needle guide 395 into the cannula housing 100, one or more sealing points may be used.

To aid in insertion of the cannula, an injector tool may be used. Injector tools may be of the type described in PCT Publication No. WO 02/100457 A2, entitled "Insertion Device for an Insertion Set and Method of Using Same,"

published Dec. 19, 2002, which is herein incorporated by reference. Injector tools are useful for patients who are reluctant or hesitant to pierce their own skin with a medical needle. The injector tool is designed to place the needle through the skin at a selected insertion angle and with a controlled force and speed of insertion to ensure proper placement with minimal discomfort.

Without being limited, several other embodiments of infusion sets comprising cannula housings and connectors, and the corresponding introducers, are described below. Because the structure of the portion of the introducer that mates with the cannula housing is the same as the portion of the connector that mates with the cannula housing, each embodiment is described with respect to the introducer and cannula housing or with respect to the connector and cannula housing. It is intended that the connector and/or introducer not described has the same mating structure as the element that is described.

Figure 7:
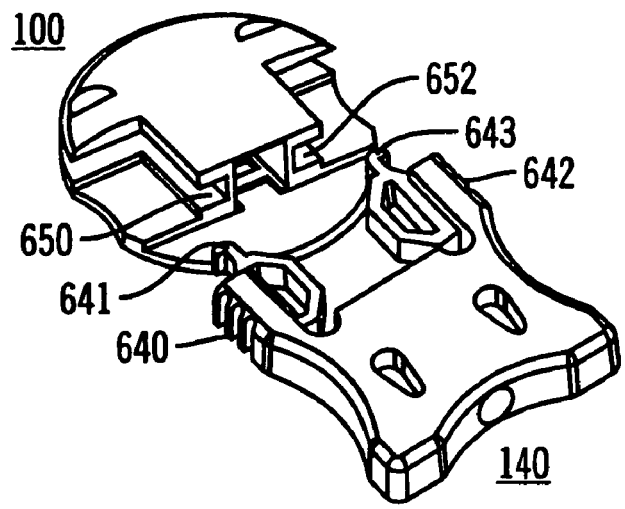
FIG. 7 is a perspective view of a cannula housing and introducer in separated form in accordance with an embodiment of the invention.

As shown in FIG. 7, in one embodiment the introducer 140 does not have guide arms that are separate from locking arms. Instead, the locking arms 640 and 642 each include barbs (641 and 643) and guide rails (644 and 645). The guide rails 644 and 645 slide into recesses 650 and 652 on the cannula housing 100.

Figure 8:
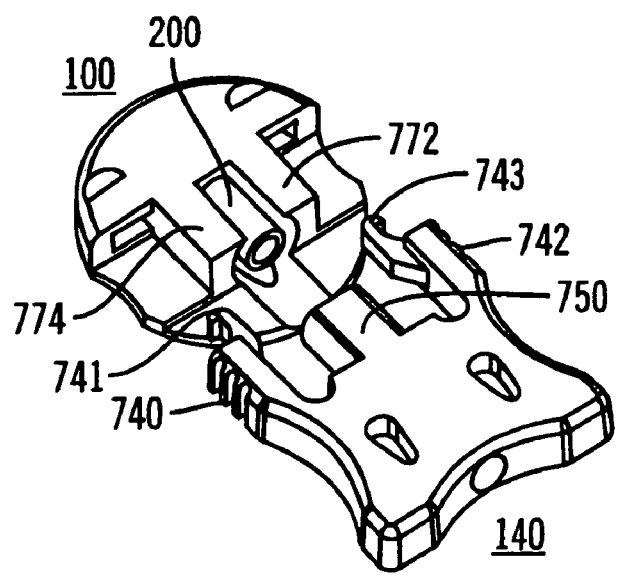
FIG. 8 is a perspective view of a cannula housing and introducer in separated form in accordance with an embodiment of the invention.

As shown in FIG. 8, in one embodiment the introducer 140 does not have guide arms. The locking arms 740 and 742 with barbs 741 and 743 are as described with respect to FIGS. 1-4. The introducer 140 includes a guide sheath 750 that closely slides over the projection 760 on the cannula housing 120 that surrounds the fluid passageway (not shown). The guide sheath 750 is also guided by two guide rails 772 and 774 that contain indentations matching the exterior of the guide sheath 750. Thus the guide sheath closely fits in between the projection 760 and the guide rails 772 and 774 to guide the introducer 140 and introducer needle (not shown) into the cannula housing 100.

Figure 9:
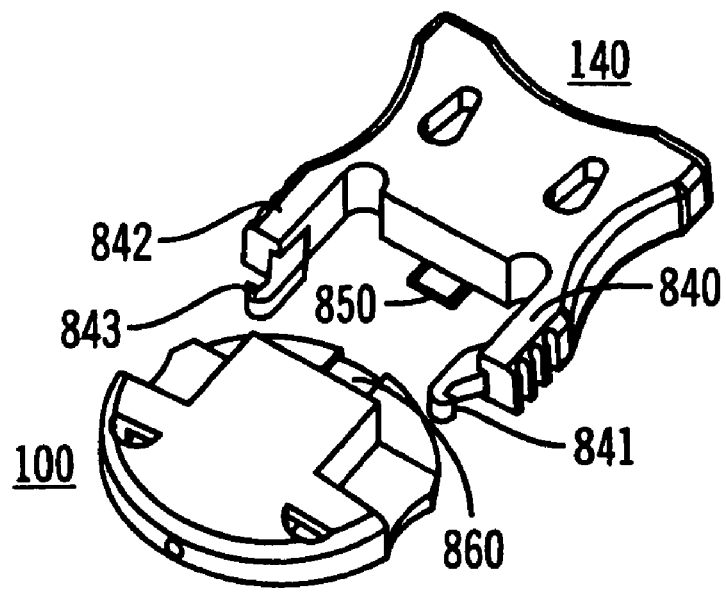
FIG. 9 is a perspective view of a cannula housing and introducer in separated form in accordance with an embodiment of the invention.

As shown in FIG. 9, in one embodiment the introducer 140 does not have guide arms. The locking arms 840 and 842 with barbs 841 and 843 are as described with respect to FIGS. 1-4. The introducer 140 has a dove tail 850 that mates with a cut-out 860 to guide the introducer 140 and introducer needle (not shown) into the cannula housing 100.

Figure 10:
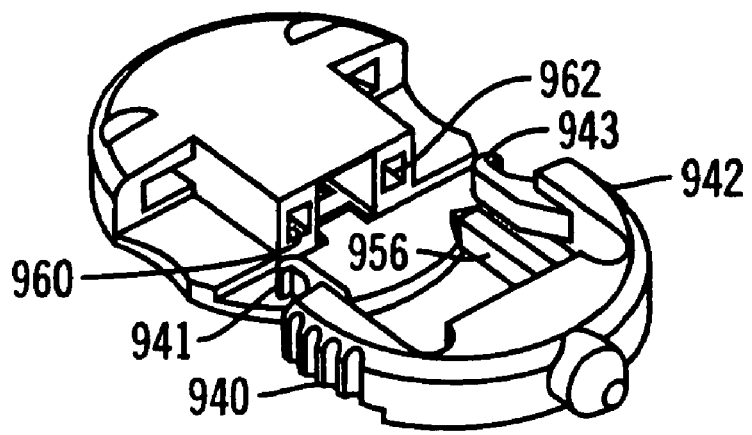
FIG. 10 is a perspective view of a cannula housing and connector in separated form in accordance with an embodiment of the invention.

As shown in FIG. 10, in one embodiment the connector 120 does not have guide arms. The locking arms 940 and 942 with barbs 941 and 943 are as described with respect to FIGS. 1-4. The connector 120 also includes a guide pin 956 that can mate with one of two guide openings 960, 962 on the cannula housing 100. As in other embodiments, the cannula housing 100 and connector 120 are preferably symmetrical, aside from the one guide pin 956, so that the user may insert the connector 120 into the cannula housing 100 regardless of which side is up. Thus, whether the one guide pin 956 will slide into a particular guide opening, 960 or 962, is dependent upon which way the connector 120 is placed with respect to the cannula housing 100. But it will be equally easy to slide the connector 120 into the cannula housing 100 in each placement.

Figure 11:
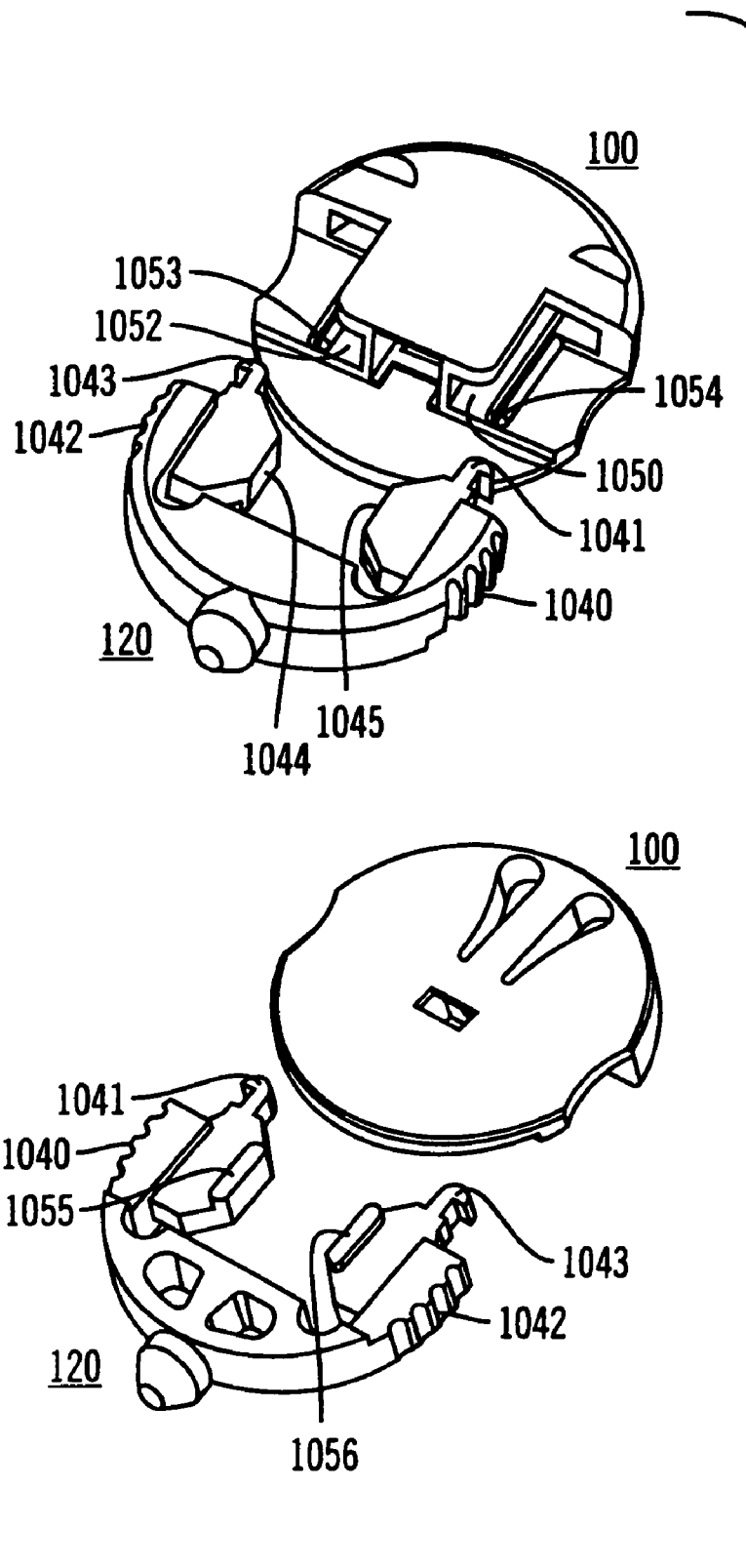
FIG. 11 is a top and a bottom perspective view of a cannula housing and connector in separated form in accordance with an embodiment of the invention.

As shown in FIG. 11, in one embodiment the connector 120 does not have guide arms. Instead, the locking arms 1040 and 1042 each include barbs (1041 and 1043) and guide rails (1044 and 1045). The guide rails 1044 and 1045 slide into recesses 1050 and 1052 on the cannula housing 100. Additionally, this embodiment may include underside rails 1053 and 1054 on the cannula housing 100, which slide alongside matching underside guide features 1055 and 1056 on the locking arms 1040 and 1042. Thus, the connector 120 is guided into the cannula housing 100 by both combinations of the guide rails 1044, 1045 and recesses 1050, 1052 and the underside rails 1053, 1054 and underside guide features 1055, 1056.

Figure 12:
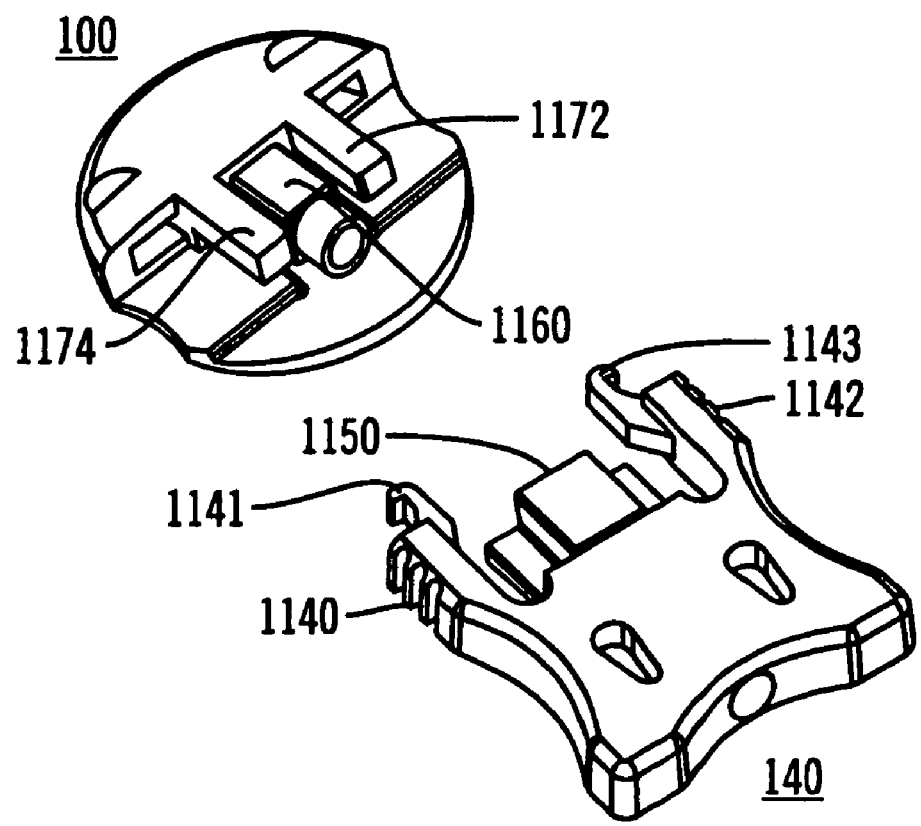
FIG. 12 is a top perspective view of a cannula housing and introducer in separated form in accordance with an embodiment of the invention.
Figure 13:
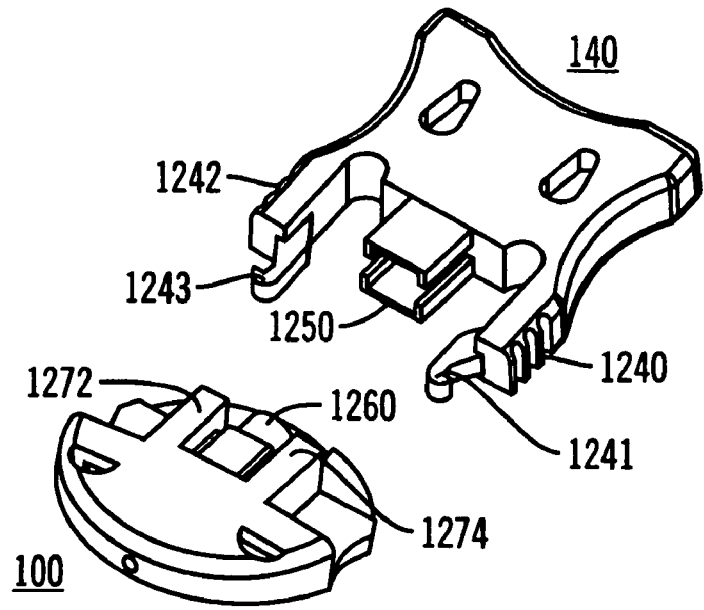
FIG. 13 is a perspective view of a cannula housing and introducer in separated form in accordance with an embodiment of the invention.
Figure 14:
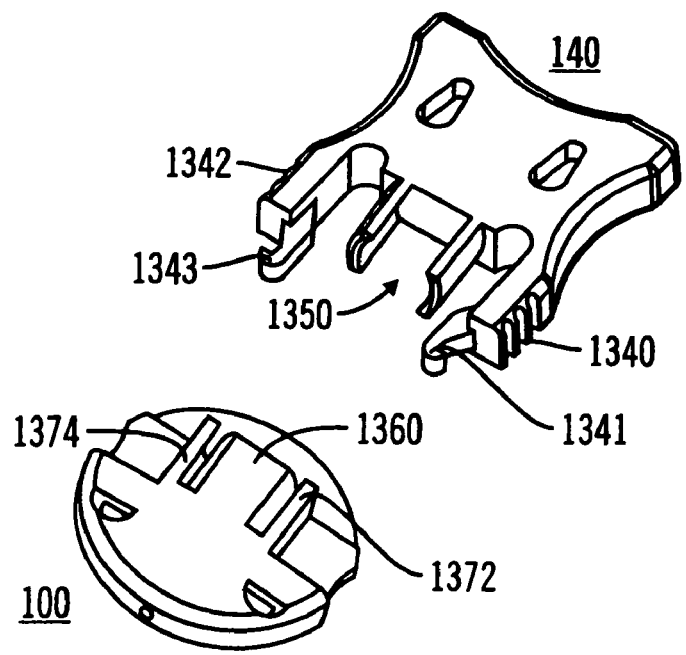
FIG. 14 is a top perspective view of a cannula housing and introducer in separated form in accordance with an embodiment of the invention.

As shown in FIGS. 12-14, in several embodiments, the introducer 140 does not have guide arms. The locking arms (1140 and 1142, 1240 and 1242, and 1340 and 1342) with barbs (1141 and 1143, 1241 and 1243, and 1341 and 1343) are as described with respect to FIGS. 1-4. The connector 120 includes a partial guide sheath which may be a half box sheath 1150, an incomplete box sheath 1250, or an incomplete oval sheath 1350. The guide sheath (1150, 1250, or 1350) closely slides over the projection (1160, 1260, or 1360) on the cannula housing 120 that surrounds the fluid passageway (not shown). The guide sheath (1150, 1250, or 1350) is also guided by two guide rails (1172 and 1174, 1272 and 1274, and 1372 and 1374) that mate with the exterior of the guide sheath (1150, 1250, or 1350). Thus the guide sheath closely fits in between the projection and the guide rails to guide the connector 120 and connector needle (not shown) into the cannula housing 100.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion set for subcutaneous administration of a fluid, comprising:
    a cannula housing defining a fluid passageway along a longitudinal axis thereof, the cannula housing including first and second guide rails and a cannula, said cannula being in fluid communication with the passageway and configured to be placed into the skin of a patient, wherein, along substantially the entire length thereof, each of said guide rails has an outer longitudinal surface with an arcuate profile; and
    a connector adapted to be connected to the cannula housing, the connector comprising separate first and second guide arms, each said guide win being configured to mate with a respective one of the guide rails, and a locking aim having a barb,
    wherein the connector is symmetrical about its longitudinal axis such that it is reversible, wherein each of the separate first and second guide arms has opposing inner and outer longitudinal sides, wherein, for each guide arm, the outer longitudinal side is flat along substantially the entire length thereof and the inner longitudinal side has an arcuate profile along substantially the entire length thereof, wherein the inner side of the first guide arm faces the inner side of the second guide arm, and wherein the cannula housing further defines a recess therein adjacent said fluid passageway, said recess being adapted to receive the barb when the connector is connected to the cannula housing.

2. The infusion set of claim 1, wherein each of said first and second guide rails is convex.

3. The infusion set of claim 1, wherein each of said first and second separate guide arms is concave.

4. The infusion set of claim 1, wherein:
the connector includes a plurality of locking arms, each said locking arm having a barb associated therewith;
the cannula housing defines a plurality of recesses; and
each said recess is adapted to receive a respective one of said barbs so as to removably connect the connector to the cannula housing.

5. The infusion set of claim 1, further comprising fluid tubing having opposing first and second ends, wherein the first end is connected to the connector and the second end is adapted to be connected to a fluid delivery device.

6. The infusion set of claim 5, wherein the fluid delivery device is an infusion pump.

7. The infusion set of claim 1, wherein at least one of the connector and the cannula housing is made of material selected from the group consisting of polycarbonate and polypropylene.

8. The infusion set of claim 1, further comprising a self-sealing septum at an end of the fluid passageway opposite the cannula.

9. The infusion set of claim 8, wherein the connector further includes a connecting needle mounted thereon and configured to pierce the self-sealing septum.

10. The infusion set of claim 9, wherein the cannula housing further includes a needle guide configured to guide the connecting needle into the fluid passageway.

11. A cannula housing for subcutaneous administration of a fluid, said housing comprising:
a projection defining a passageway therethrough;
a cannula in fluid communication with the passageway and configured to be placed into the skin of a patient;
first and second guide rails formed on an external surface of the projection, wherein, along substantially the entire length thereof, each of said guide rails has an outer longitudinal surface with an arcuate profile that mates with a respective one of a plurality of separate guide arms of a connecting device, wherein the connecting device further includes a plurality of locking arms extending outwardly therefrom, each said locking arm having a barb associated therewith; and
a plurality of recesses, each said recess being adapted to receive a respective one of said barbs.

12. The cannula housing of claim 11, wherein each said guide arm has opposing inner and outer longitudinal sides, wherein, for each guide arm, the outer longitudinal side is flat along substantially the entire length thereof and the inner longitudinal side has an arcuate profile along substantially the entire length thereof, and the inner side of the first guide arm faces the inner side of the second guide arm.

13. The cannula housing of claim 11, wherein each said recess is configured to receive a respective one of the barbs so as to removably connect the connecting device to the cannula housing.

14. The cannula housing of claim 11, wherein each of said guide rails is convex.

15. The cannula housing of claim 11, wherein each of said separate guide arms is concave.

16. The cannula housing of claim 11, wherein the connecting device includes a first guide arm that has a first concave portion and a second guide arm that has a second concave portion facing the first concave portion.

17. An infusion set for subcutaneous administration of a fluid, comprising:
a cannula housing defining a fluid passageway along a longitudinal axis thereof, the cannula housing including first and second guide rails and a cannula, said cannula being in fluid communication with the passageway and configured to be placed into the skin of a patient, wherein, along substantially the entire length thereof, each of said guide rails has an outer longitudinal surface with an arcuate profile; and
a connector adapted to be connected to the cannula housing, the connector comprising separate first and second guide arms, each said guide arm being configured to mate with a respective one of the guide rails, and a plurality of locking arms, each said locking aim having a barb associated therewith,
wherein each of the separate first and second guide arms has opposing inner and outer longitudinal sides, wherein, for each guide arm, the outer longitudinal side is flat along substantially the entire length thereof and the inner longitudinal side has an arcuate profile along substantially the entire length thereof, wherein the inner side of the first guide arm faces the inner side of the second guide arm, and wherein the cannula housing further defines a plurality of recesses therein adjacent said fluid passageway, each said recess being adapted to receive a respective one of said barbs so as to removably connect the connector to the cannula housing.

18. The infusion set of claim 17, wherein each of said first and second guide rails is convex.

19. The infusion set of claim 17, wherein each of said first and second separate guide arms is concave.

20. The infusion set of claim 17, further comprising fluid tubing having opposing first and second ends, wherein the first end is connected to the connector and the second end is adapted to be connected to a fluid delivery device.

21. The infusion set of claim 20, wherein the fluid delivery device is an infusion pump.

22. The infusion set of claim 17, wherein at least one of the connector and the cannula housing is made of material selected from the group consisting of polycarbonate and polypropylene.

23. The infusion set of claim 17, further comprising a self-sealing septum at an end of the fluid passageway opposite the cannula.

24. The infusion set of claim 23, wherein the connector further includes a connecting needle mounted thereon and configured to pierce the self-sealing septum.

25. The infusion set of claim 24, wherein the cannula housing further includes a needle guide configured to guide the connecting needle into the fluid passageway.

* * * * *